United States Patent [19]

Erickson et al.

[11] Patent Number: 4,634,682

[45] Date of Patent: Jan. 6, 1987

[54] RADIOIMMUNOASSAYS FOR THE SERUM THYMIC FACTOR (FTS)

[75] Inventors: Bruce W. Erickson, Closter, N.J.; Kam-Fook Fok; Genevieve S. Incefy, both of New York, N.Y.; Kazuhiro Ohga, Tokyo, Japan

[73] Assignee: Sloan-Kettering Institute for Cancer, New York, N.Y.

[21] Appl. No.: 737,177

[22] Filed: May 23, 1985

Related U.S. Application Data

[63] Continuation of Ser. No. 445,382, Nov. 30, 1982, abandoned.

[51] Int. Cl.⁴ .................. G01N 33/543; G01N 33/544
[52] U.S. Cl. ..................................... 436/518; 436/528; 436/542; 436/545; 436/804; 436/548; 436/822; 530/300; 530/328
[58] Field of Search ............... 436/518, 528, 542, 545, 436/548, 804, 822; 530/300, 328

[56] References Cited

U.S. PATENT DOCUMENTS

| | | | |
|---|---|---|---|
| 4,002,602 | 1/1977 | Goldstein | 260/112.5 R |
| 4,055,633 | 10/1977 | Goldstein | 424/1.1 |
| 4,124,700 | 11/1978 | Goldstein | 436/545 |
| 4,167,557 | 9/1979 | Goldstein | 436/545 |
| 4,264,571 | 4/1981 | Goldstein et al. | 436/545 |

FOREIGN PATENT DOCUMENTS

| | | | |
|---|---|---|---|
| 0041019 | 12/1981 | European Pat. Off. | 436/545 |
| 0043247 | 1/1982 | European Pat. Off. | 436/545 |
| 2407471 | 5/1979 | France | 436/545 |

OTHER PUBLICATIONS

Auger et al, Chemical Abstracts, vol. 97 (1982) #4358y.
Gastinel et al, Biochemical et Bio Physica Acta, vol. 684 (1982) pp. 117-126.

*Primary Examiner*—Christine M. Nucker
*Attorney, Agent, or Firm*—Felfe & Lynch

[57] ABSTRACT

Radioimmunoassays for the quantitation of serum thymic factor (FTS), a thymic peptide hormone, are disclosed. Each assay employs an antibody specific for FTS, the monoclonal antibody or the antibody from the antiserum of a host animal; synthetic FTS or FTS analogue as the hormone standard; and a radiolabeled FTS analogue as the tracer. Also disclosed is a method of treating serum or other biological fluid prior to assay of FTS to remove interfering substances.

10 Claims, No Drawings

RADIOIMMUNOASSAYS FOR THE SERUM THYMIC FACTOR (FTS)

This is a continuation under 37 CFR 1.60 of prior application Ser. No. 445,382, filed Nov. 30, 1982 abandoned.

This invention relates to radioimmunoassays of serum thymic factor (facteur thymique serique, FTS) a thymic peptide hormone.

BACKGROUND OF THE INVENTION

Serum thymic factor (facteur thymique serique, FTS) is a thymic hormone that induces in vitro differentiation of T-cell precursors into more mature cells with T-cell characteristics (Incefy et al., Clin. Exp. Immunol. 40, 396 (1980), Bach et al. Bull. Inst. Pasteur 76, 325 (1978)). FTS is reported to be present in the thymus (Monier et al., Clin. Exp. Immunol. 42, 470 (1980)) and its presence in serum requires the presence of the thymus (Dardenne et al., Immunology 27, 299 (1974)). As isolated from porcine serum, FTS is a nonapeptide of the amino acid sequence Glp-Ala-Lys-Ser-Gln-Gly-Gly-Ser-Asn.

The amino terminus is blocked by a pyroglutamic acid (Glp) residue (Bach et al., Nature, 226, 55 (1977); Dardenne et al., J. Biol. Chem. 252, 8040 (1977), Pleau et al., J. Biol. Chem. 252, 8045 (1977). FTS in human serum occurs as the zinc complex, thymulin (Dardenne et al., C.R. Acad. Sci. (Paris) 292, 793 (1981)).

FTS activity is detectable in the circulating blood of man and animals by a bioassy called the rosette inhibition assay (Incefy et al., Clin. Exp. Immunol. 40, 396 (1980); Iwata et al., Am. J. Med. 71, 383 (1981). The amount of FTS activity detected by this assay generally reflects thymic development and function. Other thymic hormones, such as thymopoietin (Iwata et al., Biochem. Biophys. Res. Comm. 88, 1419 (1979) and thymosin-$\alpha_1$ (Wong and Merrifield, Biochemistry 19, 3238 (1980) and certain of its segments (Ciardelli, et al. Biochemistry 21, 4233 (1982)) as well as an allogenic factor from activited T-cells (Dardenne et al. Immunology 33, 643 (1977), also show activity in the rosette inhibition assay. Thus a specific method for quantitation of FTS is needed to define the physiological and pathological characteristics of FTS, especially in vivo.

A radioimmunoassay (RIA) specific for FTS is one such useful technique for quantitation of this nonapeptide, however development of this technique has not been possible due to lack of antibodies specific for FTS and due to unavailability of suitable radioactive tracers. Recently, a monoclonal antibody against FTS (MA-FTS) using standard hybridoma technology was generated (Ogha et al., Clin. Exp. Immunol., 47, 725 (1982), U.S. patent application Ser. No. 305,579). This antibody specifically binds to synthetic FTS as well as to the substance in peripheral human blood that is detected in the rosette inhibition assay and is therefore useful in the assay of FTS. Radiolabeled analogues, however, have not been previously available because native porcine FTS lacks a phenolic ring through which a radiolabel can be attached.

SUMMARY OF THE INVENTION

Accordingly, it is a principle object of the present invention to provide antibodies for use in radioimmunoassay of FTS.

It is another object of the invention to provide analogues of FTS which may be radiolabeled by methods known in the art.

It is a particular object of the present invention to provide a method of radioassay of FTS and its naturally occuring metal (such as zinc) complex in human serum.

The method of the present invention discloses four radioimmunoassays (RIA) for the quantitation of serum thymic factor (facteur thymique serique, FTS), a thymic peptide hormone. Each assay employs an antibody specific for FTS, synthetic FTS as the hormone standard, and a radioiodinated FTS analogue as the tracer. Since FTS lacks the tyrosine residue necessary for iodination, FTS analogues were synthesized by the solid-phase method with tyrosyl-alanyl or 3-(2,6-dichlorobenzyl)tyrosyl-alanyl in place of the amino-terminal pyroglutamyl residue. These analogues show full FTS immunoreactivity and their radioiodinated derivatives serve as FTS tracers. Assays may use the antiserum from a rabbit immunized with an FTS-protein conjugate or a monoclonal antibody against FTS.

All four RIAs are specific for FTS. FTS in its naturally occuring forms, for example the zinc complex, thymulin may also be determined by the RIA of the present invention. It is to be understood that term "FTS" as hereinafter employed is meant to include FTS as well as these naturally occuring forms.

FTS analogues are disclosed which contain a residue preferrably tyrosine which can be radioiodinated. The radiolabeled analogues maintain antigenic activity against the known antibodies and are thus tracers in the radioassay of the present invention. A method for preparing these analogues and their use in RIA is disclosed.

By means of the radioimmunoassay of the present invention, FTS in solution or in biological fluids (serum and thymus extracts) may be measured. A method of treating serum prior to assay to remove interfering substances is given.

DETAILED DESCRIPTION OF THE INVENTION

Radioimmunoassays

The radioimmunoassays (RIA) for FTS may be performed by a competition method in which unlabeled FTS, other peptide, or protein competes with a radiolabeled FTS analogue for binding to an anti-FTS antibody (mouse MA-FTS or rabbit antiserum). Other RIA procedures wherein antibody is bound to a solid support are also included within the method of the present invention.

In the preferred embodiment of the present invention, a 50-$\mu$l aliquot of the anti-FTS antibody solution [mouse ascitic fluid containing MA-FTS diluted 1:60 with BSA-PBS (0.25% bovine serum albumin in 0.05M phosphate-buffered saline at pH 7.2) or rabbit antiserum diluted 1:60,000 in BSA-PBS] is added to a polystyrene tube (10×75 mm) chilled in ice. Unlabeled peptide (0.01–100 nmol for MA-FTS, 0.001–10 pmol for rabbit antiserum) in 50 $\mu$l of BSA-PBS is added and the tube is agitated briefly with a vortex mixer. Then 10,000 cpm of $^{125}$I-labeled FTS analogue in 50 $\mu$l of BSA-PBS is added and the resulting antibody/tracer/peptide solution (150 $\mu$l) is kept at 4° C. for 48 hrs. Finally, 550 $\mu$l of 3.6% bovine serum in PBS and then 700 $\mu$l of saturated ammonium sulfate in distilled water are added to precipitate the antigen-antibody complex. The tube is centrifuged at 2000×g for 30 min at 20° C. and the supernatant is removed by aspiration.

The radioactivity, R, of the precipitate may be measured in counts per minutes (cpm) using a gamma counter. The proportion of the radiolabeled peptide that is bound to the precipitated antibody in the presence of the unlabeled peptide is calculated as $$B=(R-R_b)/(R_t-R_b),$$

where $R_b$ is the background radioactivity of the precipitate when the antibody is omitted from a control tube and $R_t$ is the total radioactivity added to each tube. Similarly, the proportion of the radiolabeled peptide that precipitated in the absence of the unlabeled peptide is calculated as $$B_o=(R_o-R_b)/(R_t-R_b),$$

where $R_o$ is the radioactivity of the precipitate when the unlabeled peptide is omitted. Finally, the normalized percentage of radiolabel bound is calculated as $$\% \text{ bound}=100\times B/B_o.$$

Dose-response curves were obtained by plotting % bound versus the amount of unlabeled peptide present in the 150-μl volume of the antibody/tracer/peptide solution. A convenient measure of the ability of the unlabeled peptide to compete with the radiolabeled tracer for the FTS-binding sites on the antibody is $I_{50}$, the amount of unlabeled peptide in the antibody/tracer/peptide solution at which 50% of the tracer is bound.

The availability of two sources of anti-FTS antibodies (monoclonal antibody from mouse ascitic fluid containing MA-FTS and rabbit antiserum) and two highly $^{125}$I-labeled FTS analogues allow four different RIA systems for FTS. Synthetic FTS competes with the binding of both radiolabeled peptides to both antibodies in a dose-dependent manner.

Anti-FTS Antibodies

A monoclonal antibody directed against FTS (MA-FTS) was obtained from a hybridoma generated by fusion (Köhler and Milstein, Nature 256, 495 (1975)) of the mouse myeloma cells P3-NSI-1 Ag4-1 and spleen cells from a BALB/c mouse that had been immunized with synthetic FTS coupled through 1% glutaraldehyde to mouse IgG (Ohga et al., supra, 1982). The hybridoma was maintained in tissue culture. Ascitic fluid containing MA-FTS was withdrawn 2 weeks after intraperitoneal injection of 2×10$^7$ hybridoma cells into pristane-primed BALB/c mice. Preparation of this monoclonal antibody is disclosed in co-pending application, Ser. No. 365,579.

Rabbit anti-FTS antiserum was drawn from a New Zealand white rabbit that had been immunized with synthetic FTS coupled with 1% glyceraldehyde to F(ab')$_2$ fragments of rabbit IgG. This serum was the most active of the sera from six rabbits so treated, each of which contained anti-FTS antibody as measured by an enzyme-linked immunosorbent assay.

FTS Analogues

The amino acid sequence of native porcine FTS is as follows:

Glp-Ala-Lys-Ser-Gln-Gly-Gly-Ser-Asn-OH wherein Glp is pyroglutamic acid, Ala is alanine, Lys is lysine, Ser is serine, Gln is glutamine, Gly is glycine, and Asn is asparagine. Since there is no phenolic ring in any of these amino acids, FTS cannot be radioiodinated directly. Accordingly, derivatives of FTS containing a phenolic ring have been synthesized by replacing terminal pyroglutamic acid with alanine and attaching tyrosine to the latter.

Preferred compounds comprise the FTS decapeptide analogues of the following formula:

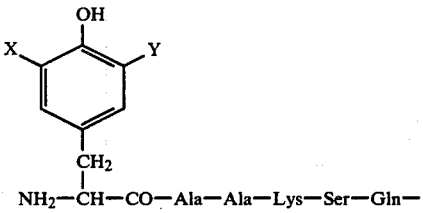

—Gly—Gly—Ser—Asn—OH wherein X and T are both hydrogen (Compound I) or X is hydrogen and Y is dichlorobenzyl (Compound II). It is to be understood, however, that other tyrosyl derivatives of FTS are likewise within the scope of the present invention. Thus, for example the tyrosine may be substituted at other positions of the aromatic ring with groups such as methyl, ethyl, halogen, or cyano and at the αamino group with groups such as methyl, ethyl, benzyl, acetyl, propianyl, benzoyl, methanesulfonyl, benzenesulfonyl or toluenesulfonyl. In addition, the α-aminos group may be replaced by hydrogen.

Likewise, blocking group Y in preferred embodiments may be substituents of the formula:

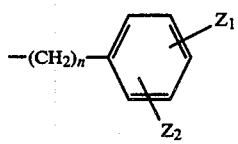

wherein n is an integer from 1 to 4 and $Z_1$ and $Z_2$ are each hydrogen or halogen. Finally, one or both alanine residues may be replaced by other amino acids or may be omitted from the preferred compounds.

Preferred compounds I and II were synthesized by the solid-phase method (Erickson and Merrifield, in: "The Proteins," 3rd Ed., Vol. 2, eds. H. Neurath and R. L. Hill, Jr. (Academic Press, New York) p. 255 (1976)) using a manually controlled shaker. α-Aminobenzylcopoly(styrene-1% divinylbenzene) (2 g, 0.56 mmol NH$_2$/g, 1.0 equivalent) was neutralized by stirring for 10 min with triethylamine/CH$_2$Cl$_2$ (1:3, v/v; 50 ml). The NH$_2$-resin was washed with five portions of CH$_2$Cl$_2$, suspended in CH$_2$Cl$_2$ (50 ml) containing N-Boc-aspartic acid α-benzyl ester and N,N''-dicyclohexylcarbodiimide (DCC) (3.4 mmol, 3.0 equivalents each), shaken for 12 h and sequentially washed using 50-ml portions 3 times with CH$_2$Cl$_2$, twice each with ethanol, CH$_2$Cl$_2$, dimethylformamide, and ethanol, and 5 times with CH$_2$Cl$_2$. Unreacted amino groups were acetylated for 2 h with acetic anhydride and pyridine (20 ml each). The Boc-Asp(NH-resin)-OBzl contained 0.30 mmol Asp/g resin.

Nine amino acid residues were added using 25 ml of liquid per gram of resin by repeating the following 5-step synthetic cycle. Step 1: deprotection of the Boc-peptide-resin (1.0 equivalent) with trifluoroacetic acid/CH$_2$Cl$_2$ (1.1, v/v) for 1 minute and 30 minutes followed by washing 4 times with CH$_2$Cl$_2$, twice with 2-propanol, and 5 times with CH$_2$Cl$_2$. Step 2: neutralization with 3 portions of diisopropylethylamine/CH$_2$Cl$_2$ (1:19, v/v) for 2 minutes each followed by washing 5 times with CH$_2$Cl$_2$. Step 3: coupling for 1 hour with the next Boc-amino acid and DCC (3 equivalents each) followed by washing 3 times with CH$_2$Cl$_2$, twice each with 2-propanol, CH$_2$Cl$_2$, and 2-propanol, and 5 times with CH$_2$Cl$_2$. Steps 4 and 5: repetition of Steps 2 and 3. After Step 5, the extent of coupling was monitored by picric acid titration (Gisin, *Anal. Chim. Acta* 58, 248 (1972)); additional coupling steps were not necessary. For coupling of Boc-glutamine, Step 3 was modified as follows. Boc-glutamine and 1-hydroxybenzotriazole (4 equivalents each) in dimethylformamide were mixed at 0° C. for 10 minutes. DCC (4 equivalents) in CH$_2$Cl$_2$ was precooled to 0° C. and added to the mixture. After 10 minutes the mixture was filtered and the filtrate was shaken with the peptide resin for 1 hour. The resin was washed 3 times with CH$_2$Cl$_2$, twice each with 2-propanol, CH$_2$Cl$_2$, 2-propanol, and 5 times with CH$_2$Cl$_2$.

Peptides were cleaved from the resin by treatment with anhydrous HF/4-cresol (9:1, v/v) for 30 min, during which the reaction mixture was warmed from −70° C. to 0° C. After evaporation of the HF, the resin was washed with ether and peptides were eluted with acetic acid/water (1, v/v). After the eluate was concentrated to 5 ml and lyophilized to dryness, the residue was suspended in acetic acid/water (1:4, v/v) and centrifuged for 2 min to remove insoluble material. The supernatant was purified by reverse-phase chromatography on a stainless-steel column (0.78×30 cm) containing octadecyl-silica (μBondapak C$_{18}$, Waters Associates, Milford, MA). Peptides were eluted with a 15-min linear gradient of 0–60% methanol in 0.05% trifluoroacetic acid/water at 2 ml/minute and continuously monitored by ultraviolet absorption at both 220 and 250 nm. The following two decapeptides were purified to homogeneity by rechromatography on the same reverse-phase column.

L-Tyrosyl-L-alanyl-FTS-(2-9). This major decapeptide (I) was eluted from the reverse-phase column as a single peak at 11.6 min, gave a single spot on TLC (R$_f$ (A) 0.29, (B) 0.20, (C) 0.19), showed satisfactory molar ratios for the expected amino acids after acid hydrolysis (Asp 1.03, Ser 1.90, Gln 1.03, Gly 2.01, Ala 4.97, Tyr 0.99, Lys 0.96), exhibited the expected (M+Na)$^+$ ion (m/e calculated 1004.44, found 1004.76), and showed the proper NMR pattern for the aromatic protons (6.96 (2H, d 7.5) and 7.20 ppm (2H, d 7.5)). 3-(2,6-Dichlorobenzyl)-L-tyrosyl-L-alanyl-FTS-(2-9). This minor decapeptide (II) was eluted from the reverse-phase column as a single peak at 19.3 min, gave a single sport on TLC (R$_f$(A) 0.49, (B) 0.45, (C) 0.37), provided satisfactory amino acid molar ratios (Asp 1.01, Ser 1.98, Glu 1.03, Gly 1.97, Ala 1.97, Tyr 0.00, Lys 1.04), showed the correct (M+Na)$^+$ ion (m/e calculated 1162.41, found 1162.98), and exhibited the expected NMR patterns for the aromatic protons (6.82 (1H, s), 7.09 (1H, d 7.5) and 7.25 ppm (1H, d 7.5) for the phenolic ring and 7.07 (1H, t 8.2) and 7.40 ppm (2H, d 8.2) for the dichlorophenyl ring). This modified peptide was formed by migration of the 2,6-dichlorobenzyl protecting group of tyrosine from the phenolic oxygen to an ortho carbon of the phenolic ring during HF treatment (Erickson and Merrifield, *J. Am. Chem. Soc.* 95, 3750 (1973)).

Radiolabeling of FTS peptides

The synthetic peptide analogues of FTS bear the residues Tyr-Ala and Tyr(Cl$_2$Bzl)-Ala, respectively, in place of the amino-terminal pyroglutamic acid residue present in FTS. These phenolic rings were directly radioiodinate by the chloramine-T method (Hunter and Greenwood, *Nature* 194, 495 (1962)) to provide the radioiodinated linear decapeptides of the formula:

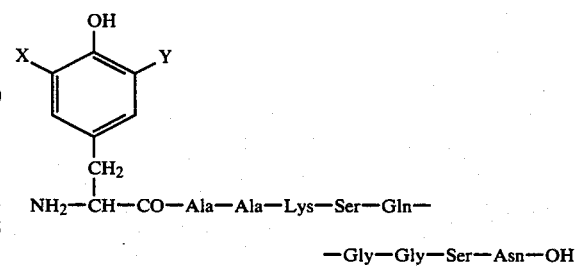

where X is $^{125}$I and Y is hydrogen (Compound III) or dichlorobenzyl, (Compound IV).

Direct radioiodination of the phenolic decapeptides I and II using carrier-free [$^{125}$I]NaI and chloramine-T (Hunter and Greenwood, *Nature* 194, 495 (1962)) for 2 min gave the $^{125}$I-labeled FTS decapeptide analogues III and IV, respectively.

Immunoreactivity of FTS analogues I and II

Radioiodinated peptides III and IV differ from porcine FTS with the replacement of Glp-1 by the dipeptides Tyr(3I)-Ala and Tyr(3-I,5-Cl$_2$Bzl)-Ala, respectively. The influence of these amino-terminal structural differences on the immunoreactivity of peptides III and IV was examined by measuring the dose-response curves in these four RIAs for peptides I and II, the noniodinated precursors of peptides III and IV. The unlabeled peptide concentration needed for 50% inhibition of labeled peptide binding (I$_{50}$) was essentially the same for both FTS and the FTS analogue I in all three RIAs examined. Similarly, the I$_{50}$ value for dichlorobenzylated analogue II was nearly the same as that for FTS in each of the RIAs using the rabbit antiserum. But the I$_{50}$ values for benzylated peptide II in the RIA's using the mouse MA-FTS and radiolabeled peptides III and IV were 3 and 23 times lower than those for FTS, respectively. Thus, the rabbit antiserum is insensitive to the presence of the amino-terminal dipeptide in the FTS analogues I and II. The monoclonal mouse antibody, however, can distinguish between the amino-terminal dipeptide of dichlorobenzylated FTS analogue II and the amino-terminal pyroglutamyl residue of FTS.

The specific activity and immunoreactivity of the radiolabeled FTS analogues given in Table I shows that the bulk (60–87%) of these $^{125}$I-labeled FTS analogues remained bound to the mouse and rabbit anti-FTS antibodies during ammonium sulfate precipitation in the absence of unlabeled peptide.

TABLE I

| Precursor | 125I Reagent | Peptide Product | Specific Activity (Ci/mmol) | Immunoreactivity[a] (%) Mouse MA-FTS | Immunoreactivity[a] (%) Rabbit antiserum |
|---|---|---|---|---|---|
| Peptide I | NaI | Peptide III | 1,200 | 61 | 60 |
| Peptide II | NaI | Peptide IV | 1,400 | 87 | 86 |

[a] Radiolabeled peptide (10,000 cpm) in 50 μl of 0.25% BSA-PBS and excess anti-FTS antibody (1:2 dilution of MA-FTS ascitic fluid; 1:200 dilution of rabbit antiserum) in 50 μl of the same buffer were incubated for 24 hr at 4° C.; precipitation with 50% ammonium sulfate was performed as described in Methods. Immunoreactivity (%) is expressed as 100 × (cpm of ammonium sulfate precipitate/total cpm added).

Sensitivity of the radioimmunoassays

The concentration of synthetic FTS (molecular weight 858) needed to decrease the binding of the radiolabeled FTS analogue to the antibody by 50% ($I_{50}$) is a useful measure of the sensitivity of a given RIA for detection of FTS. When MA-FTS was the antibody, the $I_{50}$ values for FTS were about $3.3 \times 10^{-5}$M ($5.0 \times 10^3$ pmol/150 μl) for peptide III and $4.1 \times 10^{-5}$M ($6.2 \times 10^3$ pmol/150 μl) for benzylated peptide IV as the radiolabeled standard. In contrast, when the rabbit antiserum was used as the antibody source, the $I_{50}$ values for FTS were about $7.3 \times 10^{-11}$M ($1.1 \times 10^{-2}$ pmol/150 μl) for peptide III and $1.2 \times 10^{-10}$M for benzylated peptide IV. Thus, the FTS analogues III and IV are nearly equivalent in these RIAs. But the RIAs using the rabbit antiserum are about $4 \times 10^5$ times more sensitive than those using the mouse monoclonal antibody.

The sensitivities of the RIAs using radiolabeled FTS analogue III were determined more accurately from dose-responce curves. The $I_{50}$ value for FTS using the mouse monoclonal antibody was $3.6 \times 10^{-5}$M ($5.4 \times 10^3$ pmol/150 μl of antibody/tracer/FTS solution or 4.6 ug/50 μl of the initial FTS solution). A practical lower limit for detection of FTS is the amount needed to inhibit the binding of tracer III by 10%. By this criterion, the mouse monoclonal antibody can detect the presence of as little as 0.26 μg (300 pmol) of FTS in 50 μl of the initial FTS solution. The rabbit antiserum, however, gave an $I_{50}$ value for FTS of $8.0 \times 10^{-11}$M and could detect the presence of as little as 1.0 pg ($1.2 \times 10^{-3}$ pmol) of FTS per 50-μl of the initial FTS solution.

Specificity of the radioimmunoassays

It has been observed that the biologically active form of FTS occurs as a metal complex such as the zinc complex, thymulin (Dardenne et al., *C. R. Acad. Sci. (Paris)* 292, 793 (1981)). The radioimmunoassay of the present invention is of use in quantitative measurement of thymulin.

The ability of the FTS radioimmunoassays using peptide III to detect components of thymic hormone preparations, active synthetic peptide segments from other thymic hormones, or unrelated short peptides was explored. The RIAs failed to detect synthetic thymosin-$\alpha_1$-(20-28)-nonapeptide and thymopoietin-(32-36)-pentapeptide or two unrelated nonapeptides, bradykinin and EAE peptide. In addition, neither purified interleukin-2 (15 units) nor any of the compounds present in 10-μg (dry weight) samples of the thymic extracts called leucotrofina or thymosin fraction V were detected by the RIA based on tracer III and the rabbit antiserum. Thus, these RIAs and the antibodies on which they are based are highly specific for FTS.

The fine specificity of these antibodies was explored using a dozen synthetic FTS peptide analogues having various residues replaced or omitted (Fok et al., *Mol. Immunol.* 19, 1667 (1982)). Both antibodies were very sensitive to changes or omission of residues 5-9 of porcine FTS but insensitive to replacement or omission of Glp-1 or Ala-2. Thus, these RIAs are selective for peptide chains ending in ---Xxx-Xxx-Gln-Gly-Gly-Ser-Asn-OH, where Xxx is a unspecified amino acid residue.

Radioimmunoassay of FTS in Plasma

Plasma from normal donors appeared to inhibit the binding of radiolabeled peptide III to the anti-FTS antibodies. However, it was found that plasma depleted of FTS and other small peptides by treatment with activated charcoal also appeared to inhibit binding, so the decrease in % bound of peptide III was not due to the specific competition of FTS present in plasma. Thus, the immunoreactivity of peptide III with MA-FTS was measured after incubation in various media for 0 to 24 hours. After incubation of peptide III for 24 hours in BSA-PBS containing no plasma, its immunoreactivity decreased only about 10%, but after incubation with human plasma, it decreased about 60%. Thus the decrease is apparently due to degradation of the tracer peptide III with time rather than a time-independent nonspecific inhibition of the binding of peptide III to the monoclonal antibody. This degradation with time was not decreased by the presence of the protease inhibitor aprotinin. It was found that degredation could be reduced to the background level by filtering the plasma through an Amicon CF-50A membrane (Amicon Corp., Lexington Mass.), which normally excludes proteins with molecular weights above 50,000.

Standard calibration curves were determined for the RIA based on the rabbit antiserum and peptide III by using known amounts of synthetic FTS in BSA-PBS or in the CF-50A filtrates of FTS-free plasma. The latter was prepared by mixing the plasma from a healthy 78-year old donor with activated charcoal (100 mg/ml) for 2 h at 4° C. and centrifuging for 30 min at 2,000×g. The supernatant was passed through an 0.22-μ filter to remove fine particles and filtered through a CF-50A membrane by centrifugation. The RIA used the rabbit antiserum, tracer peptide III, and known amounts of synthetic porcine FTS.

The calibration curves were nearly superimposable indicating that the sensitivity of this RIA is just as high for determining the amount of FTS present in CF-50A filtered plasma samples as in a plasma-free medium. Thus, this RIA detected the presence of 2.2 pg of FTS in 50 μl of CF-50A filtrate from the plasma of a normal 5-year-old boy, which corresponds to a plasma FTS concentration of 44 pg/ml.

What is claimed is:

1. Radioimmunoassay of serum thymic factor (FTS) in a test sample, comprising:
   (a) contacting a first aliquot of said sample with anti-FTS antibody, with a known amount of FTS hormone standard and a known amount of radiolabeled FTS analogue; and
   (b) contacting a second aliquot of said sample with anti-FTS antibody and a known amount of radiolabeled FTS analogue; and
   (c) measuring the radioactivity of the antigen-antibody complex in each aliquot; and (d) calculating the amount of FTS in the test sample, wherein the hormone standard and the radiolabeled analogue are of the formula

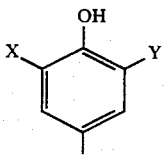

wherein X is $^{125}I$ for the radiolabeled analogue or hydrogen for the hormone standard and Y is hydrogen or a compound of the formula

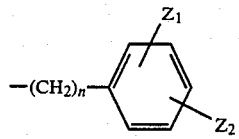

wherein n is 1 to 4 and $Z_1$ and $Z_2$ are hydrogen and/or halogen; A is hydrogen or $NH_2$; B is alanine or another amino acid; and m is an integer from zero to 2.

2. The radioimmunossay of claim 1 wherein said antibody is a monoclonal antibody.

3. The radioimmunossay of claim 1 wherein said antibody is from a mammalian antiserum to FTS.

4. The radioimmunossay of claim 1 wherein said antibody is immobilized on a solid inert support.

5. The radioimmunoassay of claim 1 wherein said synthetic hormone standard is FTS.

6. Radioimmunoassay of claim 1 wherein said test sample is a biological fluid.

7. Radioimmunoassay of claim 1 wherein said test sample is human serum.

8. Radioimmunoassay of claim 7 comprising an additional step of treating said serum to remove interfering substances prior to assay.

9. Radioimmunoassays of claim 8 wherein said substances are removed by filtration of said plasma through a membrane of controlled pore size.

10. FTS analogues having the formula:

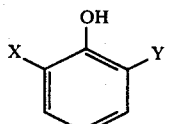

wherein X is $^{125}I$ and Y is hydrogen or a compound of the formula:

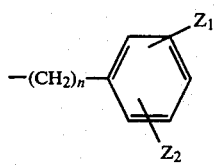

wherein n is 1 to 4 and $Z_1$ and $Z_2$ are hydrogen and/or halogen. A is hydrogen or $NH_2$; B is alanine or other amino acid; and m is an integer from zero to 2.

* * * * *